United States Patent [19]

Arnold

[11] Patent Number: 5,804,165
[45] Date of Patent: Sep. 8, 1998

[54] ANTIPLAQUE ORAL COMPOSITION

[76] Inventor: Michael J. Arnold, 791 Newton Way, Costa Mesa, Calif. 92627

[21] Appl. No.: 685,703

[22] Filed: Jul. 24, 1996

[51] Int. Cl.⁶ .............................. A61K 7/16; A61K 9/46; A61K 9/20; A61K 9/48
[52] U.S. Cl. .............................. 424/44; 424/49; 424/465; 424/466; 424/452; 424/464
[58] Field of Search .............................. 424/44, 465, 466, 424/49

[56] References Cited

U.S. PATENT DOCUMENTS

| | | | |
|---|---|---|---|
| 975,354 | 11/1910 | Gruter et al. .............................. | 424/49 |
| 975,814 | 11/1910 | Westlake .............................. | 424/49 |
| 1,082,681 | 12/1913 | Danner .............................. | 424/49 |
| 1,112,180 | 9/1914 | Westenfelter .............................. | 424/49 |
| 1,262,888 | 4/1918 | Westlake . | |
| 1,275,275 | 8/1918 | Levinson . | |
| 1,297,494 | 3/1919 | Rhein .............................. | 424/49 |
| 1,516,398 | 11/1924 | McDowell .............................. | 424/49 |
| 2,035,267 | 3/1936 | Fleischman .............................. | 167/93 |
| 2,218,172 | 10/1940 | Kokatnur .............................. | 167/93 |
| 2,820,000 | 1/1958 | Menzies .............................. | 424/49 |
| 2,868,655 | 1/1959 | Ladenburg .............................. | 99/143 |
| 2,951,791 | 9/1960 | Stearns .............................. | 167/82 |
| 3,087,827 | 4/1963 | Davis et al. .............................. | 167/53.2 |
| 3,101,299 | 8/1963 | Ferrand .............................. | 167/82 |
| 3,136,692 | 6/1964 | Bandelin .............................. | 167/57 |
| 3,227,521 | 1/1966 | Carithers et al. .............................. | 424/49 |
| 3,330,732 | 7/1967 | Muhler .............................. | 167/93 |
| 3,372,125 | 3/1968 | Hill .............................. | 252/99 |
| 3,431,339 | 3/1969 | Gyarmathy et al. . | |
| 3,432,338 | 3/1969 | Sickles . | |
| 3,488,288 | 1/1970 | Hill .............................. | 252/99 |
| 3,518,343 | 6/1970 | Welsh et al. .............................. | 424/44 |
| 3,518,344 | 6/1970 | Welsh et al. .............................. | 424/44 |
| 3,518,345 | 6/1970 | Welsh et al. .............................. | 424/44 |
| 3,574,824 | 4/1971 | Echeandia et al. .............................. | 424/50 |
| 3,577,490 | 5/1971 | Welsh et al. .............................. | 264/120 |
| 3,577,492 | 5/1971 | Welsh et al. .............................. | 264/120 |
| 3,629,468 | 12/1971 | Andersen .............................. | 424/44 |
| 3,670,076 | 6/1972 | Muhler .............................. | 424/157 |
| 3,767,791 | 10/1973 | Gordon et al. .............................. | 424/49 |
| 3,772,431 | 11/1973 | Mlkvy et al. .............................. | 424/52 |
| 3,821,117 | 6/1974 | Breece et al. .............................. | 252/99 |
| 3,888,976 | 6/1975 | Mlkvy et al. .............................. | 424/44 |
| 3,914,434 | 10/1975 | Bohnl .............................. | 424/243 |
| 3,932,604 | 1/1976 | Barth .............................. | 424/49 |
| 3,935,305 | 1/1976 | Delaney et al. .............................. | 424/49 |
| 3,937,321 | 2/1976 | Delaney et al. .............................. | 206/84 |
| 3,937,803 | 2/1976 | Delaney et al. .............................. | 424/49 |
| 3,937,804 | 2/1976 | Delaney et al. .............................. | 424/52 |
| 3,962,417 | 6/1976 | Howell .............................. | 424/52 |
| 3,976,601 | 8/1976 | Levin . | |
| 4,062,793 | 12/1977 | Schödel .............................. | 252/99 |
| 4,127,645 | 11/1978 | Witzel et al. .............................. | 424/44 |
| 4,155,868 | 5/1979 | Kaplan et al. .............................. | 252/95 |
| 4,157,386 | 6/1979 | La Rochelle . | |
| 4,180,467 | 12/1979 | Barth .............................. | 252/99 |
| 4,181,621 | 1/1980 | Raaf et al. .............................. | 252/102 |
| 4,267,164 | 5/1981 | Yeh et al. .............................. | 424/44 |
| 4,302,441 | 11/1981 | Mühlmann et al. .............................. | 424/48 |
| 4,308,252 | 12/1981 | Tomaich et al. . | |
| 4,367,218 | 1/1983 | Jacobson . | |
| 4,411,885 | 10/1983 | Barels et al. . | |
| 4,414,198 | 11/1983 | Michaelson .............................. | 424/44 |
| 4,487,757 | 12/1984 | Kiozpeoplou .............................. | 424/7.1 |
| 4,528,180 | 7/1985 | Schaeffer .............................. | 424/52 |
| 4,537,778 | 8/1985 | Clipper et al. .............................. | 424/53 |
| 4,592,487 | 6/1986 | Simon et al. .............................. | 222/94 |
| 4,627,972 | 12/1986 | Gioffre et al. .............................. | 424/44 |
| 4,647,451 | 3/1987 | Piechota, Jr. .............................. | 424/52 |
| 4,753,792 | 6/1988 | Aberg . | |
| 4,818,518 | 4/1989 | Gioffre et al. .............................. | 424/44 |
| 4,832,956 | 5/1989 | Geroely et al. .............................. | 424/466 |
| 4,923,685 | 5/1990 | Wuelknitz et al. .............................. | 424/54 |
| 4,971,782 | 11/1990 | Rudy et al. .............................. | 424/53 |
| 4,980,154 | 12/1990 | Gordon et al. .............................. | 424/53 |
| 4,983,379 | 1/1991 | Schaeffer .............................. | 424/52 |
| 5,000,941 | 3/1991 | Chernack .............................. | 424/49 |
| 5,008,106 | 4/1991 | Merianos et al. .............................. | 424/80 |
| 5,028,414 | 7/1991 | Sampathkumar .............................. | 424/53 |
| 5,057,305 | 10/1991 | Aberg . | |
| 5,122,365 | 6/1992 | Murayama .............................. | 424/49 |
| 5,204,115 | 4/1993 | Olinger et al. .............................. | 424/271 |
| 5,571,441 | 11/1996 | Andon et al. .............................. | 252/1 |

FOREIGN PATENT DOCUMENTS

| | | |
|---|---|---|
| 284579 | 12/1963 | Australia . |
| 20 40 999 A | 3/1971 | Germany . |
| 2051499 | 4/1971 | Germany . |
| 1259342 | 2/1969 | United Kingdom . |
| 1269620 | 10/1970 | United Kingdom . |
| WO 88 10110 A | 12/1988 | WIPO . |
| WO 92 07550 A | 5/1992 | WIPO . |

OTHER PUBLICATIONS

*Cosmetics & Toiletries*, May 1982, "Dentifrices: Perspectives", by Morton pader, vol. 97, pp. 40–58.

J. Soc. Cosmet. Chem., 29, 497–521 (Aug. 1978), "Cosmetics Properties and Structure of Fine Particle Synthetic Precipitated Silicas", by S.K. Wason, pp. 497–521.

*Primary Examiner*—Shep K. Rose
*Attorney, Agent, or Firm*—Lyon & Lyon LLP

[57] ABSTRACT

Disclosed is a non-liquid oral dentifrice composition commonly in the form of powder or tablets which is characterized by an efficacious ratio of carbon dioxide source, xylitol, acid source and silicon dioxide.

8 Claims, No Drawings

ANTIPLAQUE ORAL COMPOSITION

I. FIELD OF THE INVENTION

The present invention relates to the field of oral health care preparations, and more specifically to improved oral health care preparations comprising anhydrous, solid, effervescent compositions.

II. BACKGROUND OF THE INVENTION

Sodium bicarbonate, baking soda, has been used for centuries as an aid to clean the human mouth and for the deodorizing and freshening the breath. In vitro scientific studies have shown that the bicarbonate ion has mild but significant antimicrobial properties against specific bacterial species, in particular anaerobic bacterial species, many of which have been shown to cause periodontal diseases (Newbrun E., et.al. J. Periodontal. 55, 11, 658-657, 1984). Compositions of baking soda and dilute hydrogen peroxide have been prescribed as a preventative and mild remedial treatment for gingivitis and periodontal diseases. (Randal, J. E., A. H. 2, 82—82, 1982, Rudy et al., U.S. Pat. No. 4,971,782). For example, the Keyes technique, named after Dr. Keyes from the National Institute of Health (NIH), is a common preventative and remedial treatment for mild to moderately severe cases of periodontitis. The Keyes technique can employ baking soda and dilute solutions of hydrogen peroxide. These agents are combined by simply dipping a toothbrush into a 1.5% to 3% hydrogen peroxide solution followed immediately by spreading the peroxide-wetted toothbrush through a bed of baking soda and applying it to the teeth with a brushing motion. A major shortcoming of this method is the foul taste, as well as the resultant gum irritation. Another Keyes method uses a thick paste made of baking soda powder in combination with 1.5% to 3% hydrogen peroxide. The paste is applied directly to the surface of the teeth and gums and maintained there for extended periods of time (on the order of a few minutes to less than an hour). However, laymen can have difficulty in preparing this paste and the compound gives rise to discomfort as a result of its foul taste and long residence time required to realize efficacy.

Many modern-age toothpaste compositions also use baking soda as the chief ingredient, presumably to add to the plaque reducing and breath deodorizing properties of the dentifrice. However, oral preparations containing the bicarbonate ion as the active component have heretofore not been demonstrated to have significant effectiveness, that is they have not been reported to show significant bactericidal properties in vivo.

Halitosis (oral malodor) has also been an unsolved physiological problem for centuries, and remains as such in the modern era. The chemical basis of halitosis lies in the concentration of mouth-bound volatile and odiferous compounds, primarily organic and inorganic sulfides as well as organic amines. These odiferous volatiles are biologically synthesized by particular microorganisms that reside in the oral cavity. Halitosis is primarily caused by certain anaerobic strains of bacteria (Rosenberg, M., *Bad Breath: Research Perspectives*, Ramot Publishing, 1995). Specifically, the proliferation in saliva of the anaerobic bacterial pathogen *Fusobacterium* Species, in combination with other anaerobes, have been shown as the major biological source of halitosis. Chemical mouthwash treatments have been recommended to treat halitosis, such as dilute solutions of chlorine dioxide, which presumably act as an oxidizing agent to rid of oral sulfides. A major shortcoming of this method is the unproven long term safety of the chlorine dioxide solution (bleach). Since a significant amount of the chlorine dioxide is absorbed through the mouth tissue and is sometimes ingested, implementation of the mouthwash into the daily practice raises serious questions of safety.

Effervescent oral compositions have been taught in several US patents dating from about 1914 to the present. For example, U.S. Pat. No. 1,297,494 is directed to an effervescent, solid dentifrice comprising an acid salt and a bicarbonate salt which mutually react in the presence of moisture to produce $CO_2$ and an initially weak acid solution which contacts the surface of the teeth. Howell, U.S. Pat. No. 3,962,417, teaches an effervescent dentifrice for treatment against caries. Yeh, U.S. Pat. No. 4,267,164 teaches an effervescent oral composition for the convenient and effective delivery of fluoride ion to the oral cavity. Welsh, U.S. Pat. No. 3,518,343 teaches an effervescent mouthwash tablet composition as a tablet form, where the binder is a specific combination of ingredients.

The prior art mentioned above teaches that combinations of baking soda and organic acids (typically fruit acids) begin to immediately effervesce when placed in the oral cavity, thereby chemomechanically removing plaque and food debris during effervescence.

Although bicarbonate based mouthwashes or solid dentifrice products have been taught, none have been demonstrated as bonafide in vivo bactericidal agents. Moreover, none have been proven to significantly effect an improvement to the health of the gingiva or for conditioning of the breath.

A further shortcoming of the prior art is the inherent instability of the effervescent compositions, since the self-sustaining effervescent reaction takes place rapidly with water thus causing commercial embodiments to be inherently unstable. This in turn results in the composition having an unacceptable shelf life unless it is prepared and securely packaged in an inert environment. Further, compositionally, the prior art compounds lack antimicrobial efficacy and have a poor taste, usually chalky or salty. The problems of developing a dentifrice which has both good taste and efficacy is crucial since frequent use of the composition is important to long term regulation of gingivitis and periodontitis. Finally, the plaque reducing properties of compositions in the prior art are minimal, since no plaque adsorption mechanism is provided.

III. SUMMARY OF THE INVENTION

The present invention solves these problems by uniquely formulating blends of bicarbonate salts with adsorbent silicone dioxide polymers; (b) teaching a novel mechanistic mode of action, plaque adsorption, underlying plaque reducing properties; (c) providing for the inherent stability of dentifrice compositions thereby improving shelf life; and, (d) substantially improving the flavor and cleansing sensation while maintaining efficacy, thereby creating a unique biologically active dentifrice which tastes good and is fun to use. Resulting widespread consumer compliance significantly decreases the amount of periodontal disease, and creates a novel treatment for halitosis that is both discrete and efficacious.

The present invention is directed towards non-aqueous oral compositions comprising a pharmaceutically acceptable form of bicarbonate salt, or carbonate salt, or combinations thereof; an amorphous silica; and a form of xylitol.

In addition to xylitol, other naturally occurring co-sweeteners can be employed, such as dextrose, mannitol, sorbitol, fructose, and maltose. In addition the artificial sweeteners saccharin, aspartame, neohesperidin dihydrochalcone, and others known to the art may also be used in combination with the xylitol to enhance the sweetening and flavoring properties of the xylitol. Malto dextrin may also be used in the present invention to sweeten as well as enhance the flow and compression properties of the various compositions of the present invention, since these compositions are often powders that are subjected to manufacturing processes commonplace in the art of commercial and pharmaceutical mass production.

The relative amounts of xylitol, an anti-caries agent available from American Xyofin, to the bicarbonate and silica is important to the improved efficacy of the present invention. First, the present invention's ability to control the growth of Streptococcus mutans is enhanced in comparison to the use of oral preparations using xylitol exclusively for caries prevention. This enhanced anti-streptococcus effect results because pH is controlled over time by a proper amount of bicarbonate-silicon dioxide complex. Second, even though xylitol alone is an effective bactericidal agent for Streptococcus mutans, its activity against the anaerobic pathogens is poor unless it is combined with a proper amount of bicarbonate ion and silicon dioxide. It is the control of the growth of these anaerobic pathogens which is important for the prevention of gingivitis, periodontitis and halitosis. Too much xylitol, alone or in combination with co-sweeteners, significantly reduces the dentifrice's activity against these anaerobic pathogens. However, it is also important to impart to the consumer the desire to use the product of the invention twice to thrice daily in order to fully realize the bactericidal properties as well as plaque and odor reducing properties. Within these parameters (as discussed below) suitable mixtures of xylitol with other flavor agents are also within the scope of the invention.

The composition also contains a non-aqueous pharmaceutically acceptable acid source selected from the group consisting of organic acids, such as citric acid, tartaric acid, fumaric acid, malic acid, and partial salts of these acids or mixtures thereof. The composition can optionally include a non-aqueous excipient, a non-aqueous pharmaceutically acceptable anti-bacterial agent, and about 0.3 to 30 percent by weight of a pharmaceutically acceptable hydrogen peroxide source.

Sufficient bicarbonate or carbonate salt is employed in the composition so that in an aqueous pH test mixture of the composition, the acid or the acid salt is completely neutralized by the bicarbonate or carbonate salt, and that an excess of the bicarbonate or carbonate salt is employed such that a basic pH of the aqueous solution (>7), is maintained from minimum of 1 minute to about 1 hour, or greater, depending on the patient and specific composition of the present invention that is employed.

The composition can be administered as a tablet, as a powder, and as a capsule which is dispersible in human saliva. The inventor's method for preparation of bicarbonate-silicon dioxide compositions incorporates a method of pharmaceutical processing named granulation. Polyvinylpyrrolinone can be used in the present invention as the preferred granulating agent because it aids in binding the silicon dioxide polymer to the bicarbonate salt.

The plaque removal and anti-plaque properties of the composition are not fully understood. It is believed that when the composition is placed in the oral cavity, the saliva wets the composition dissolving the bicarbonate or carbonate salt and the solubilized bicarbonate or carbonate ion and the acid components in the resulting saliva mixture undergo a rapid acid-base reaction generating carbon dioxide gas (effervescence). The resulting salivary solution is swept through the oral cavity, between the teeth, into crevices and cavities in between the teeth and into the juncture of the gums and teeth. It is believed that the bicarbonate or carbonate ion, the acid, acid salt components, and the acid-bicarbonate and carbonate salt components chemically loosen the plaque and other organic debris from the surface of the teeth, possibly via a debriding type of action. The effervescent action of the saliva sweeps a portion of the loosened plaque and organic and inorganic debris from the surfaces of the teeth and gums. After the effervescence has stopped, the resulting saliva mixture can be swished through the mouth to cleanse the surfaces of the teeth and gums (especially the surfaces between adjoining teeth) and to sweep out loose organic and inorganic debris. After expulsion or swallowing, it is believed that an appreciable amount of the solid bicarbonate-silica material adheres to the proteinaceous debris and mucosa which naturally resides on the surfaces of the teeth and gums. Consequently, the bicarbonate-silica complexes of the present invention are sustained in the oral cavity from minutes to hours. As a direct result of this sustansivity, plaque is adsorbed over time by the silica particles (adsorbents).

Furthermore, sodium bicarbonate (or other bicarbonate salt) is released to the saliva over time. Accordingly, the present invention causes an enhanced bacteriocidal action arising from the sustained release of the bicarbonate ion. A speculated mechanism for this action is as follows: Residual solid bicarbonate salt starts to dissolve immediately after swallowing, or expulsion of, the original salivary mixture. Over time (seconds to many minutes), bicarbonate salt desorbs from the sustained plaque-bound silica-bicarbonate material. This latent solubilization of the bicarbonate salt results in a substantial amount of bicarbonate ion present in the salivary mixture. Of significance, studies have shown (see, e.g., Newbrun, E.; Bactericidal Action of Bicarbonate on Selected Periodontal Pathogenic Microorganisms, J. Periodontal, 55, 11, 653, 1984), that if left in the oral cavity for over 15 minutes, concentrated solutions of bicarbonate ion have appreciable bacteriocidal action against bacteria that cause periodontal disease. Since the bicarbonate ion is sustained in the oral cavity the salivary solutions generated are mildly bacteriocidal and, hence, provide the user with a novel, effective and chemically active therapeutic treatment for preventing and treating gingivitis, periodontal diseases and halitosis.

It is an object of the present invention to provide a dry oral wash composition that can be inserted into the oral cavity following a meal, snack, coffee or the smoking of a cigarette in order to rinse the mouth free of organic debris and inhibit the formation of plaque.

Another object of the present invention is to provide and anti-plaque composition that will inhibit the build-up of plaque on the teeth and inhibit the population growth of plaque bacteria in the oral cavity.

It is a further object of the present invention to provide a good tasting efficacious oral composition that is safe for human consumption and that will be used regularly by individuals in preventing gingivitis and periodontal disease.

It is a further object of the present invention to provide effervescent oral compositions that are capable of adsorbing plaque biomass.

It is a further object of the present invention to provide effervescent oral compositions that are effective in limiting the growth of odor causing bacteria.

It is a further object of the present invention to provide oral compositions which neutralize the acids in the oral cavity and to effect a sustained neutral pH of the saliva (above pH of 7 for minutes after swallowing or expulsion).

DETAILED DESCRIPTION OF THE INVENTION

Bicarbonate ion is combined with certain silicon dioxide polymers in the present invention, at specific rations. In the present invention, a range of 1 to 10 parts bicarbonate ion to 1 part silicone dioxide is preferred, a range of 1 to 5 parts bicarbonate ion to 1 part silica is more preferred, and a range of 2 to 4 parts bicarbonate ion to 1 part silica is most preferred. The form of silicone dioxide suitable for use in the present invention is amorphous silica, while precipitated amorphous silica is preferred, and precipitated amorphous silica having a low amount of aluminum (between 0.1% and 2%) is most preferred. The most preferred silica is named ZEO-49 and is commercially available from J. M. Huber. The same ratios hold true if a carbonate is used instead of bicarbonate.

The bicarbonate-silicone dioxide preparations of the present invention may be free flowing blends, or most preferably, as granulated mixtures milled to a size that will pass through a sieve #20 to a sieve #80. The preferred granulating agent is polyvinylpyrrolinone (PVP) (Kollidone 30 [BASF]). The preferred solvent of granulation is water, although other solvents and granulating agents known to the art of pharmaceutical manufacturing can be employed for the preparation of the bicarbonate-silicon dioxide preparation in the present invention. The amount of granulating agent is important, since an excess will inhibit the clinical efficacy of the present invention by inactivating the plaque adsorption and sustainment properties of the xylitol-bicarbonate-silicone dioxide oral preparation. The range of granulating agent is about 1–30 parts PVP to 100 parts bicarbonate-silicone dioxide preparation, and preferably from about 3 to 15 parts PVP to 100 parts bicarbonate-silicon dioxide preparation and most preferably from about 3 to 7 parts PVP to 100 parts bicarbonate-silicon dioxide preparation.

As explained earlier, the relative amounts of xylitol to the bicarbonate ion-silicon dioxide preparation is important. A ratio of xylitol to bicarbonate-silicon dioxide of about 0.5 parts to 7 parts xylitol to 3 parts bicarbonate-silicon dioxide preparation is preferred, and a ratio of about 1.0 to 5 parts xylitol to 3 parts bicarbonate-silicon dioxide preparation is more preferred, and the ratio of about 2 to 4 parts xylitol to 3 parts bicarbonate-silicon dioxide preparation is the most preferred.

Fructose, dextrose, sorbitol, mannitol, and others, referred to here as natural co-sweeteners, are not critical, but may also be used to enhance the sweetening characteristics of the present invention. The amounts of these natural co-sweeteners to the amount of xylitol are from about 1 to 60 parts co-sweetener to 30 parts xylitol, and from about 1.5 parts to 40 parts co-sweetener to 30 parts xylitol, and most preferably from about 2 to 10 parts co-sweetener to 30 parts xylitol.

Sweetening agents, both artificial and natural, having a sweetness much greater than sucrose, may also be employed as co-sweeteners to enhance the flavoring characteristics of the present invention. The most preferred artificial sweeteners are aspartame, saccharin, or neohesperidin dihydrochalcone, although others known to the art may also be employed. The preferred ranges for these sweetening agents is from 1 part sweetener to about 0.1 part to 50 parts xylitol, and from about 1 part sweetener to about 0.5 part to 25 parts xylitol, and most preferably from about 1 part to about 5 parts sweetener to about 10 parts to about 15 parts xylitol.

The fruit acids such as citric acid, tartaric acid, fumaric acid, and malic acid may also be employed in the present invention. Citric acid is preferred. The amount of fruit acid is 1 part fruit acid to about 1 to about 20 parts bicarbonate ion, and preferably about 1 part fruit acid to about 1.5 to 10 parts bicarbonate ion and most preferably from about 1 part fruit acid to about 1.5 part to 5 parts bicarbonate ion. If a carbonate source is used in place of bicarbonate, the amount of fruit acid should be adjusted accordingly to maintain pH of neutral or greater in test solution. For example, the amount of fruit acid is 1 part fruit acid to about 1 to 20 parts bicarbonate ion, and preferably about 1 part fruit acid to about 1.5 to 10 parts bicarbonate ion and most preferably from about 1 part fruit acid to about 1.5 part to 5 parts bicarbonate ion.

EXAMPLES

The following examples are intended to illustrate, but not to limit the present invention.

Example 1:

| Ingredient | mass (Kg) |
| --- | --- |
| xylitol (American Xyofin) | 1401 |
| mannitol | 250 |
| aspartame (Nutrasweet) | 135 |
| sodium lauryl sulfate (Witco) | 20 |
| 1 - menthol crystals | 25 |
| mint flavoring | 3.6 |
| sodium-bicarbonate (FMC #1) | 1250 |
| Silica (ZEO-49 [J. M. Huber Co.]) | 410 |
| Citric Acid (anhydrous crystals) | 243 |

The above are admixed in a rotating blender, and blended for at least 30 minutes under conditions of low shear, to produce an effervescent oral composition in powder form.

Example 2:

This example describes Applicant's preferred embodiment.

| Ingredient | mass (Kg) |
| --- | --- |
| xylitol (American Xyofin) | 1401 |
| mannitol | 250 |
| aspartame (Nutrasweet) | 135 |
| sodium lauryl sulfate (Witco) | 20 |
| 1 - menthol crystals | 25 |
| mint flavoring | 3.6 |
| sodium bicarbonate (FMC #1) | 1250 |
| silica (ZEO-49 [J. M. Huber Co.]) | 410 |
| citric Acid (anhydrous crystals) | 243 |
| polyvinyl pyrrolinone (PVP K-30 [FMC]) | 89 |
| magnesium stearate | 20 |
| stearic acid | 6.5 |

In a separate batch mixer, the sodium bicarbonate, silicone dioxide, sodium lauryl sulfate, are admixed, and to this is added a lukewarm solution of 89 Kg of polyvinylpyrrolinone (PVP) in 593 Kg of distilled water, and then this was mixed until a homogeneous cake was formed. This cake was spread evenly onto trays and dried in an oven at less than 225° C. until completely dry (<1% moisture). This dried cake was then pulverized to a particle size of between 40 mesh and 100 mesh sieve. The powder was kept separate from the blend of the other components until the time of mixing. The blending process requires that the sodium bicarbonate-silicone dioxide powder admixed in portions over about 1 to 2 hours in a tumble blender (or other blender of low shear) to insure complete blending without the destruction of the binding properties of the blend. The powder is immediately pressed into tablets.

Example 3:

This example describes a biologically active composition with a peroxide source, which is incorporated to enhance the biological activity as well as cosmetic tooth whitening.

| Ingredient | mass (Kg) |
| --- | --- |
| xylitol (American Xyofin) | 1560 |
| mannitol | 280 |
| aspartame (Nutrasweet) | 145 |
| sodium lauryl sulfate (Witco) | 20 |
| 1 - menthol crystals | 31 |
| mint flavoring | 3.8 |
| sodium bicarbonate (FMC #1) | 1276 |
| urea hydrogen peroxide (Robeko, N. Y.) | 305 |
| silica (ZEO-49 P. M. Huber Co.]) | 418 |
| citric Acid (anhydrous crystals) | 253 |
| polyvinyl pyrrolinone (PVP K-30 [FMC]) | 89 |
| magnesium stearate | 20 |
| stearic acid | 85 |

The sodium bicarbonate, silicon dioxide, PVP, sodium lauryl sulfate are prepared in a separate batch as mentioned in example 2. This and the remaining above ingredients are admixed in a rotating blender, and blended for at least 30 minutes under conditions of low shear, to produce a powder that can be tableted using a Stokes table press.

Example 4:

This example describes a biologically active composition with a chlorine dioxide source, which is incorporated to enhance the biological activity, and for the treatment of halitosis.

| Ingredient | mass (Kg) |
| --- | --- |
| xylitol (American Xyofin) | 1560 |
| mannitol | 180 |
| sorbitol | 126 |
| aspartame (Nutrasweet) | 125 |
| sodium lauryl sulfate (Witco) | 20 |
| chlorine dioxide source | 2.5% |
| I - menthol crystals | 35 |
| mint flavoring | 4.1 |
| sodium bicarbonate (FMC #1) | 1276 |
| silica (ZEO-49 [J. M. Huber Co.]) | 418 |
| citric Acid (anhydrous crystals) | 253 |
| polyvinyl pyrrolinone (PVP K-30 [FMC]) | 89 |
| magnesium stearate | 20 |
| stearic acid | 85 |

The sodium bicarbonate, silicon dioxide, PVP, sodium lauryl sulfate are prepared in a separate batch as mentioned in example 2. This and the remaining above ingredients are admixed in a rotating blender, and blended for at least 30 minutes under conditions of low shear, to produce a powder that can be tableted using a Stokes table press.

Example 5:

This example describes a biologically active composition with a Iodine source, which is incorporated to enhance the biological activity.

| Ingredient | mass (Kg) |
| --- | --- |
| xylitol (American Xyofin) | 1560 |
| mannitol | 280 |
| aspartame (Nutrasweet) | 145 |
| sodium lauryl sulfate (Witco) | 20 |
| 1 - menthol crystals | 31 |
| mint flavoring | 3.8 |
| Povidone Iodine | 33% |
| sodium bicarbonate (FMC #1) | 1276 |
| urea hydrogen peroxide (Robeko, N. Y.) | 305 |
| silica (ZEO-49 [J. M. Huber Co.]) | 418 |
| citric Acid (anhydrous crystals) | 253 |
| polyvinyl pyrrolinone (PVP K-30 [FMC]) | 89 |
| magnesium stearate | 20 |
| stearic acid | 85 |

The sodium bicarbonate, silicon dioxide, PVP, sodium lauryl sulfate are prepared in a separate batch as mentioned in example 2. This and the remaining above ingredients are admixed in a rotating blender, and blended for at least 30 minutes under conditions of low shear, to produce a powder that can be tableted using a Stokes table press.

Example 6:

This example describes a highly biologically active composition with a chlorhexidine source, which is incorporated to enhance the biological activity.

| Ingredient | mass (Kg) |
| --- | --- |
| xylitol (American Xyofin) | 1560 |
| mannitol | 280 |
| aspartame (Nutrasweet) | 145 |
| sodium lauryl sulfate (Witco) | 20 |
| 1 - menthol crystals | 31 |
| mint flavoring | 3.8 |
| sodium bicarbonate (FMC #1) | 1276 |
| chlorhexidine gluconate | 14.5 |
| silica (ZEO-49 [J. M. Huber Co.]) | 418 |
| citric Acid (anhydrous crystals) | 253 |
| polyvinyl pyrrolinone (PVP K-30 [FMC]) | 89 |
| Neohesperidin dihydrochalcone (Exime) | 6 |
| magnesium stearate | 20 |
| stearic acid | 85 |

The sodium bicarbonate, silicon dioxide, PVP, sodium lauryl sulfate are prepared in a separate batch as mentioned in example 2. This and the remaining above ingredients are admixed in a rotating blender, and blended for at least 30 minutes under conditions of low shear, to produce a powder that can be tableted using a Stokes table press.

Example 7:

This example describes a new example.

| Ingredient | mass (Kg) |
| --- | --- |
| xylitol (American Xyofin) | 1401 |
| sorbitol | 125 |
| dextrose | 145 |
| aspartame (Nutrasweet) | 128 |
| sodium lauryl sulfate (Witco) | 20 |
| 1 - menthol crystals | 21 |
| mint flavoring | 3.6 |
| sodium bicarbonate (FMC#1) | 1225 |
| silica (ZE0-49 [J. M. Huber Co.]) | 401 |
| citric Acid (anhydrous crystals) | 238 |

-continued

| Ingredient | mass (Kg) |
| --- | --- |
| polyvinyl pyrrolinone (PVP K-30 [FMC]) | 82 |
| magnesium stearate | 15 |
| stearic acid | 71 |

In a separate batch mixer, the sodium bicarbonate, silicone dioxide, sodium lauryl sulfate, are admixed, and to this is added a lukewarm solution of 89 Kg of polyvinylpyrrolinone (PVP) in 593 Kg of distilled water, and then this was mixed until a homogeneous cake was formed. This cake was spread evenly onto trays and dried in an oven at less than 225° C. until completely dry (<1% moisture). This dried cake was then pulverized to a particle size of between 40 mesh and 100 mesh sieve. The powder was kept separate from the blend of the other components until the time of mixing. The blending process requires that the sodium bicarbonate-silicone dioxide powder admixed in portions over about 1 to 2 hours in a tumble blender (or other blender of low shear) to insure complete blending without the destruction of the binding properties of the blend. The powder is immediately pressed into tablets.

Example 8:

| Ingredient | mass (Kg) |
| --- | --- |
| xylitol (American Xyofin) | 140 |
| mannitol | 1800 |
| dextrose | 700 |
| aspartame (Nutrasweet) | 135 |
| sodium lauryl sulfate (Witco) | 20 |
| 1 - menthol crystals | 25 |
| mint flavoring | 3.6 |
| sodium bicarbonate (FMC #1) | 1250 |
| Silica (ZEO-49 [J. M. Huber Co.]) | 410 |
| Citric Acid (anhydrous crystals) | 243 |

The above are admixed in a rotating blender, and blended for at least 30 minutes under conditions of low shear, to produce an effervescent oral composition in powder form.

Example 9:

This example describes a new example.

| Ingredient | mass (Kg) |
| --- | --- |
| xylitol (American Xyofin) | 950 |
| fructose | 600 |
| mannitol | 307 |
| aspartame (Nutrasweet) | 100 |
| sodium lauryl sulfate (Witco) | 20 |
| 1 - menthol crystals | 27 |
| mint flavoring | 2.9 |
| sodium bicarbonate (FMC#1) | 1250 |
| silica (ZEO-49 [J. M. Huber Co.]) | 310 |
| silica (DeGusa) | 52 |
| citric Acid (anhydrous crystals) | 205 |
| tartaric acid | 53 |
| polyvinyl pyrrolinone (PVP K-90 [FMC]) | 61 |
| magnesium stearate | 20 |
| stearic acid | 80 |

In a separate batch mixer, the sodium bicarbonate, silicone dioxide, sodium lauryl sulfate, are admixed, and to this is added a lukewarm solution of 89 Kg of polyvinylpyrrolinone (PVP) in 593 Kg of distilled water, and then this was mixed until a homogeneous cake was formed. This cake was spread evenly onto trays and dried in an oven at less than 225° C. until completely dry (<1% moisture). This dried cake was then pulverized to a particle size of between 40 mesh and 100 mesh sieve. The powder was kept separate from the blend of the other components until the time of mixing. The blending process requires that the sodium bicarbonate-silicone dioxide powder admixed in portions over about 1 to 2 hours in a tumble blender (or other blender of low shear) to insure complete blending without the destruction of the binding properties of the blend. The powder is immediately pressed into tablets.

Example 10:

| Ingredient | mass (Kg) |
| --- | --- |
| xylitol (American Xyofin) | 1250 |
| mannitol | 250 |
| fructose | 280 |
| sorbitol | 292 |
| neohesperidin dihydrochalcone (NDHC Exquinne [Spain]) | 2 |
| sodium lauryl sulfate (Witco) | 20 |
| 1 - menthol crystals | 25 |
| mint flavoring | 3.6 |
| sodium bicarbonate (FMC #1) | 1250 |
| Silica (ZEO-49 [J. M. Huber Co.]) | 410 |
| Citric Acid (anhydrous crystals) | 243 |

The above are admixed in a rotating blender, and blended for at least 30 minutes under conditions of low shear, to produce an effervescent oral composition in powder form.

Example 11:

| Ingredient | mass (Kg) |
| --- | --- |
| xylitol (American Xyofin) | 250 |
| maltodextrin | 493 |
| avisil pH 102 (FMC) | 628 |
| aspartame (Nutrasweet) | 118 |
| sodium lauryl sulfate (Witco) | 20 |
| 1 - menthol crystals | 25 |
| mint flavoring | 3.6 |
| sodium bicarbonate (FMC#5) | 1250 |
| silica (ZEO-49 [J. M. Huber Co.]) | 410 |
| malic Acid (anhydrous crystals) | 243 |
| polyvinyl pyrrolinone (PVP K-30 [FMC]) | 89 |
| magnesium stearate | 20 |
| stearic acid | 65 |

In a separate batch mixer, the sodium bicarbonate, silicone dioxide, sodium lauryl sulfate, are admixed, and to this is added a lukewarm solution of 89 Kg of polyvinylpyrrolinone (PVP) in 593 Kg of distilled water, and then this was mixed until a homogeneous cake was formed. This cake was spread evenly onto trays and dried in an oven at less than 225° C. until completely dry (<1% moisture). This dried cake was then pulverized to a particle size of between 40 mesh and 100 mesh sieve. The powder was kept separate from the blend of the other components until the time of mixing. The blending process requires that the sodium bicarbonate-silicone dioxide powder admixed in portions over about 1 to 2 hours in a tumble blender (or other blender of low shear) to insure complete blending without the destruction of the binding properties of the blend. The powder is immediately pressed into tablets.

Example 12:

| Ingredient | mass (Kg) |
| --- | --- |
| xylitol (American Xyofin) | 1401 |
| mannitol | 250 |
| natural honey powder | 790 |
| sodium lauryl sulfate (Witco) | 20 |
| 1 - menthol crystals | 25 |
| mint flavoring | 3.6 |
| potassium bicarbonate | 290 |
| sodium bicarbonate (FMC #1) | 1320 |
| Silica (ZEO-49 [J. M. Huber Co.]) | 496 |
| Citric Acid (anhydrous crystals) | 243 |
| tartaric acid | 72 |

The above are admixed in a rotating blender, and blended for at least 30 minutes under conditions of low shear, to produce an effervescent oral composition in powder form.

Example 13:

This example describes Applicant's preferred embodiment for a mint candy composition.

| Ingredient | mass (Kg) |
| --- | --- |
| xylitol (American Xyofin) | 1401 |
| mannitol | 250 |
| sorbitol | 375 |
| aspartame (Nutrasweet) | 108 |
| 1 - menthol crystals | 25 |
| peppermint oil | 2.3 |
| sodium lauryl sulfate (Witco) | 15 |
| sodium bicarbonate (FMC#1) | 1250 |
| silica (ZEO-49 [J. M. Huber Co.]) | 410 |
| citric Acid (anhydrous crystals) | 243 |
| polyvinyl alcohol (PVA) | 103 |
| glycerin | 196 |
| polyethylenglycol (PEG-60) | 22 |

To a steam heated stainless steel kettle charged with 196 kg of anhydrous glycerin and 103 kg of PVA the mixture is stirred until an internal temperature of 80° C. is maintained. To this is added in portions, with gentle stirring, a blend of xylitol, mannitol and sorbitol and sodium lauryl sulfate. The resulting viscous slurry is stirred at between 75° C.–90° C. until a homogenous mixture is obtained. The slurry is allowed to cool while stirring to an internal temperature of 50°–60°. A blend of NaHcO$_3$, SiO$_2$, is then added followed by the citric acid. The mixture is then cooled to form a cake. This cake is cut and/or pulverized to meet packaging requirements.

Example 14:

| Ingredient | mass (Kg) |
| --- | --- |
| xylitol (American Xyofin) | 1401 |
| mannitol | 250 |
| aspartame (Nutrasweet) | 135 |
| 1 - menthol crystals | 25 |
| mint flavoring | 3.6 |
| sodium lauryl sulfate (Witco) | 20 |
| sodium bicarbonate (FMC #1) | 1250 |
| Silica (ZEO-49 [J. M. Huber Co.]) | 410 |
| Citric Acid (anhydrous crystals) | 243 |

The above are admixed in a rotating blender, and blended for at least 30 minutes under conditions of low shear, to produce an effervescent oral composition in powder form.

Example 15:

This example describes appetite suppressive breath mint.

| Ingredient | mass (Kg) |
| --- | --- |
| xylitol (American Xyofin) | 1401 |
| mannitol | 250 |
| aspartame (Nutrasweet) | 135 |
| 1 - menthol crystals | 25 |
| mint flavoring | 3.6 |
| sodium lauryl sulfate (Witco) | 20 |
| sodium bicarbonate (FMC#1) | 1250 |
| silica (ZEO-49 [J. M. Huber Co.]) | 410 |
| citric Acid (anhydrous crystals) | 243 |
| polyvinyl pyrrolinone (PVP K-30 [FMC]) | 89 |
| garcinio powder | 28 |
| magnesium stearate | 20 |
| stearic acid | 65 |

In a separate batch mixer, the sodium bicarbonate, silicone dioxide, sodium lauryl sulfate, are admixed, and to this is added a lukewarm solution of 89 Kg of polyvinylpyrrolinone (PVP) in 593 Kg of distilled water, and then this was mixed until a homogeneous cake was formed. This cake was spread evenly onto trays and dried in an oven at less than 225° C. until completely dry (<1% moisture). This dried cake was then pulverized to a particle size of between 40 mesh and 100 mesh sieve. The powder was kept separate from the blend of the other components until the time of mixing. The blending process requires that the sodium bicarbonate-silicone dioxide powder admixed in portions over about 1 to 2 hours in a tumble blender (or other blender of low shear) to insure complete blending without the destruction of the binding properties of the blend. The powder is immediately pressed into tablets.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. An effervescent tablet or capsule of effervescent powder for oral use comprising:
   a) a non-aqueous, water soluble pharmaceutically acceptable carbon dioxide source selected from the group consisting of bicarbonate salt, carbonate salt, and mixtures thereof;
   b) silica; and
   c) xylitol wherein the ratio of the weight of said xylitol to the weight of said bicarabonate and silica is between about 0.5 to 3 and about 7 to 3 and the ratio of the weight of said xylitol to said silica is less than 10 to 1.

2. An effervescent tablet or capsule of effervescent powder for oral use comprising:
   a) a non-aqueous, water soluble pharmaceutically acceptable carbon dioxide source selected from the group consisting of bicarbonate salt, carbonate salt, and mixtures thereof;
   b) silica; and
   c) xylitol wherein the ratio of the weight of said xylitol to the weight of said bicarabonate and silica is between about 1 to 3 and about 5 to 3 and the ratio of the weight of said xylitol to said silica is less than 10 to 1.

3. An effervescent tablet or capsule of effervescent powder for oral use comprising:

a) a non-aqueous, water soluble pharmaceutically acceptable carbon dioxide source selected from the group consisting of bicarbonate salt, carbonate salt, and mixtures thereof;

b) silica; and c) xylitol wherein the ratio of the weight of said xylitol to the weight of said bicarbonate and silica is between about 2 to 3 and about 4 to 3 and the ratio of the weight of said xylitol to said silica is less than 10 to 1.

4. A method for cleaning an oral cavity comprising the steps of:

a) placing into an oral cavity an effervescent tablet or capsule of effervescent powder for oral use having a non-aqueous, water soluble, pharmaceutically acceptable carbon dioxide source selected from the group consisting of bicarbonate salt, carbonate salt, and mixtures thereof; silica and xylitol wherein wherein the ratio of the weight of said xylitol to the weight of said bicarbonate and silica is between about 0.5 to 3 and about 7 to 3 and the ratio of the weight of said xylitol to said silica is less than 10 to 1;

b) solubilizing said tablet or capsule powder;

c) using the resulting saliva mixture to remove organic debris and biomass from the teeth; and d) expelling or swallowing the resulting saliva mixture.

5. A method for cleaning an oral cavity comprising the steps of:

a) placing into an oral cavity an effervescent tablet or capsule of effervescent powder for oral use having a non-aqueous, water soluble, pharmaceutically acceptable carbon dioxide source selected from the group consisting of bicarbonate salt, carbonate salt, and mixtures thereof; silica and xylitol wherein wherein the ratio of the weight of said xylitol to the weight of said bicarabonate and silica is between about 1 to 3 and about 5 to 3 and the ratio of the weight of said xylitol to said silica is less than 10 to 1;

b) solubilizing said tablet or capsule powder;

c) using the resulting saliva mixture to remove organic debris and biomass from the teeth; and d) expelling or swallowing the resulting saliva mixture.

6. A method for cleaning an oral cavity comprising the steps of:

a) placing into an oral cavity an effervescent tablet or capsule of effervescent powder for oral use having a non-aqueous, water soluble, pharmaceutically acceptable carbon dioxide source selected from the group consisting of bicarbonate salt, carbonate salt, and mixtures thereof; silica and xylitol wherein wherein the ratio of the weight of said xylitol to the weight of said bicarabonate and silica is between about 2 to 3 and about 4 to 3 and the ratio of the weight of said xylitol to said silica is less than 10 to 1;

b) solubilizing said tablet or capsule powder;

c) using the resulting saliva mixture to remove organic debris and biomass from the teeth; and d) expelling or swallowing the resulting saliva mixture.

7. An effervescent tablet or capsule of effervescent powder for oral use as in claims 1, 2 or 3 wherein the silica is amorphous silica.

8. A method for cleaning an oral cavity as in claims 4, 5 or 6 wherein the silica is amorphous silica.

* * * * *